United States Patent
Zhu

(10) Patent No.: US 11,607,164 B2
(45) Date of Patent: Mar. 21, 2023

(54) BRAINWAVE SIGNAL COLLECTING DEVICE

(71) Applicant: BOE TECHNOLOGY GROUP CO., LTD., Beijing (CN)

(72) Inventor: Lin Zhu, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 1221 days.

(21) Appl. No.: 16/085,696

(22) PCT Filed: Feb. 7, 2018

(86) PCT No.: PCT/CN2018/075542
§ 371 (c)(1),
(2) Date: Sep. 17, 2018

(87) PCT Pub. No.: WO2018/201769
PCT Pub. Date: Nov. 8, 2018

(65) Prior Publication Data
US 2020/0305750 A1 Oct. 1, 2020

(30) Foreign Application Priority Data
May 3, 2017 (CN) .......................... 201710304229.8

(51) Int. Cl.
A61B 5/00 (2006.01)
A61B 5/291 (2021.01)
(Continued)

(52) U.S. Cl.
CPC ............... A61B 5/291 (2021.01); A61B 5/30 (2021.01); A61B 5/6814 (2013.01); G06F 3/015 (2013.01)

(58) Field of Classification Search
CPC ..... A61B 5/0532; A61B 5/0536; A61B 5/168; A61B 5/6803; A61B 5/7264; A61B 5/375;
(Continued)

(56) References Cited

U.S. PATENT DOCUMENTS 3,505,993 A * 4/1970 Lewes ....................... A61N 1/04
600/382
3,534,733 A * 10/1970 Phipps .................... A61B 5/252
600/387
(Continued)

FOREIGN PATENT DOCUMENTS

CN 204207745 U 3/2015
CN 206044627 U 3/2017
(Continued)

OTHER PUBLICATIONS

Search Report and Written Opinion for International Application No. PCT/CN2018/075542 dated May 7, 2018.

Primary Examiner — Joseph A Stoklosa
Assistant Examiner — Brian M Antiskay
(74) Attorney, Agent, or Firm — Calfee, Halter & Griswold LLP

(57) ABSTRACT

A brainwave signal collecting device includes a main part and an elastic sleeve having a first opening. The main part is installed on the elastic sleeve, and the elastic sleeve can be positioned by suction on a user's head through the first opening after being pressed. The main part is in contact with the head to collect brainwave signals. The brainwave signal collecting device has an elastic sleeve serving as a flexible piece. When the brainwave signal collecting device is worn, the elastic sleeve can be pressed to partly exhaust the air therein so as to be positioned by suction on the head by the first opening of the elastic sleeve, which can improve the comfort of the head in contact with the elastic sleeve; and the (Continued)

position and angle at which the main part contacts the head can be adjusted through the deformation of the elastic sleeve.

3 Claims, 4 Drawing Sheets

(51) Int. Cl.
*G06F 3/01* (2006.01)
*A61B 5/30* (2021.01)

(58) Field of Classification Search
CPC ..... A61B 5/4806; A61B 5/291; A61B 5/4088; A61B 5/0006; A61B 5/165; A61B 5/252; A61B 5/282; A61B 5/341; A61B 5/377; A61B 5/4362; A61B 5/6814; A61B 5/6843; A61B 5/685; A61B 7/04; A61B 5/145; A61N 1/04
USPC ......... 600/372, 382–395, 508–509, 544–545
See application file for complete search history.

(56) References Cited

U.S. PATENT DOCUMENTS

| | | | | |
|---|---|---|---|---|
| 4,217,908 A | * | 8/1980 | Staver | A61B 5/252 600/387 |
| 4,550,735 A | * | 11/1985 | Akamatsu | A61B 5/282 600/386 |
| 4,640,290 A | * | 2/1987 | Sherwin | A61B 5/291 600/382 |
| 4,736,749 A | * | 4/1988 | Lundback | A61B 7/04 600/387 |
| 4,936,306 A | * | 6/1990 | Doty | A61B 5/377 600/382 |
| 5,345,935 A | * | 9/1994 | Hirsch | A61B 5/4362 600/549 |
| 6,201,982 B1 | | 3/2001 | Menkes et al. | |
| 2008/0275359 A1 | * | 11/2008 | Mintz | A61B 5/291 600/544 |
| 2009/0156925 A1 | * | 6/2009 | Jin | A61B 5/291 600/372 |
| 2011/0054288 A1 | * | 3/2011 | Besio | A61B 5/6843 600/383 |
| 2013/0102872 A1 | * | 4/2013 | Park | A61B 5/0532 600/372 |
| 2014/0316230 A1 | * | 10/2014 | Denison | A61B 5/168 600/545 |
| 2015/0265176 A1 | * | 9/2015 | Dalke | A61B 5/291 600/544 |
| 2016/0143554 A1 | * | 5/2016 | Lim | A61B 5/6803 600/386 |
| 2017/0258400 A1 | * | 9/2017 | Jovanovic | A61B 5/6814 |

FOREIGN PATENT DOCUMENTS

| | | |
|---|---|---|
| CN | 107088065 A | 8/2017 |
| JP | 2011120866 A * | 6/2011 |
| JP | 2016158964 A | 9/2016 |
| RU | 2171090 C1 | 7/2001 |

* cited by examiner

BRAINWAVE SIGNAL COLLECTING DEVICE

RELATED APPLICATIONS

The present application is a 35 U.S.C. § 371 national stage application of PCT International Application No. PCT/CN2018/075542, filed on Feb. 7, 2018, which claims the benefit of Chinese Patent Application No. 201710304229.8, filed on May 3, 2017, the contents of which are incorporated herein by reference in their entireties.

TECHNICAL FIELD

The present disclosure relates to, but is not limited to, the field of signal collecting technologies, and more particular to a brainwave signal collecting device.

BACKGROUND OF THE DISCLOSURE

In a micro-electromechanical system, a brainwave signal collecting device is a brainwave signal collecting part of a brainwave signal processing system, which is in contact with a head to collect brainwave signals. The existing brainwave signal collecting device is, however, usually secured to a head in the form of a clamping sleeve or a tightening band, which is very uncomfortable and has an unsatisfactory brainwave signal collecting effect.

SUMMARY

In view of this, the present disclosure provides a brainwave signal collecting device, comprising a main part; and an elastic sleeve having a first opening, wherein the main part is installed to the elastic sleeve, and the elastic sleeve is configured to be positioned by suction on a user head through the first opening after being pressed and make the main part in contact with the head to collect brainwave signals.

In certain exemplary embodiments, the main part comprises a brainwave signal collecting unit located in the elastic sleeve; and a brainwave signal processing unit electrically connected with the brainwave signal collecting unit.

In certain exemplary embodiments, the brainwave signal collecting unit comprises: a carbon nanotube array for collecting the brainwave signals; and a spring having two ends, wherein one end of the spring is electrically connected with the carbon nanotube array, and the other end of the spring is electrically connected with the brainwave signal processing unit.

In certain exemplary embodiments, the brainwave signal collecting unit comprises: a spring array for collecting the brainwave signals; and a first electrically conductive piece having two ends, wherein one end of the first electrically conductive piece is electrically connected with the spring array, and the other end of the first electrically conductive piece is electrically connected with the brainwave signal processing unit.

In certain exemplary embodiments, the brainwave signal collecting unit further comprises: a second electrically conductive piece installed on the spring array that collects the brainwave signals through the second electrically conductive piece.

In certain exemplary embodiments, the first electrically conductive piece and/or the second electrically conductive piece are electrically conductive electrodes, and the electrically conductive electrode comprises: an electrode body; a protective sleeve having a top wall, one end of the electrode body extending into the protective sleeve and the other end thereof being located outside the protective sleeve; a spring located in the protective sleeve and connected with the top wall of the protective sleeve and the end of the electrode body extending into the protective sleeve; and a wire with one end located externally of the protective sleeve and the other end extending through the top wall of the protective sleeve so as to be electrically connected with the end of the electrode body extending into the protective sleeve.

In certain exemplary embodiments, the first electrically conductive piece and/or the second electrically conductive piece are springs. For instance, when one of the first electrically conductive piece and the second electrically conductive piece is an electrically conductive electrode, the other one of the first electrically conductive piece and the second electrically conductive piece may be an electrically conductive spring.

In certain exemplary embodiments, the brainwave signal processing unit is a brainwave signal processing circuit, and a material of the elastic sleeve is rubber or leather.

In certain exemplary embodiments, the brainwave signal processing circuit is located inside or outside the rubber sleeve.

In certain exemplary embodiments, the rubber sleeve also has a second opening encapsulated by the brainwave signal processing circuit.

Other features and advantages of the present disclosure will be expounded in the following description, and become partly obvious from the description, or be understood through implementation of the present disclosure. The object and other advantages of the present disclosure can be realized and obtained by the structures particularly indicated in the description, claims and drawings.

BRIEF DESCRIPTION OF DRAWINGS

The drawings help to further understand the technical solutions of the present disclosure, constitute a part of the description, are used, together with the embodiments of the present disclosure, to explain the technical solutions herein, and impose no limitations to the technical solutions herein.

DETAILED DESCRIPTION

To better clarify the object, technical solutions and advantages of the present disclosure, the embodiments of the present disclosure will be explained in detail with reference to the drawings. It should be appreciated that without conflict, the embodiments and the features thereof herein can be combined at will.

Many details are expounded in the following depiction for better understanding of the present disclosure. However, the present disclosure can also be implemented by other manners not mentioned herein. Therefore, the scope of the present disclosure is not restricted by the embodiments disclosed herein.

A brainwave signal collecting device according to some embodiments of the present disclosure will be described with reference to the drawings.

The present disclosure provides a brainwave signal collecting device, which improves the usability and makes a head wearing the same more comfortable.

Figure 1:
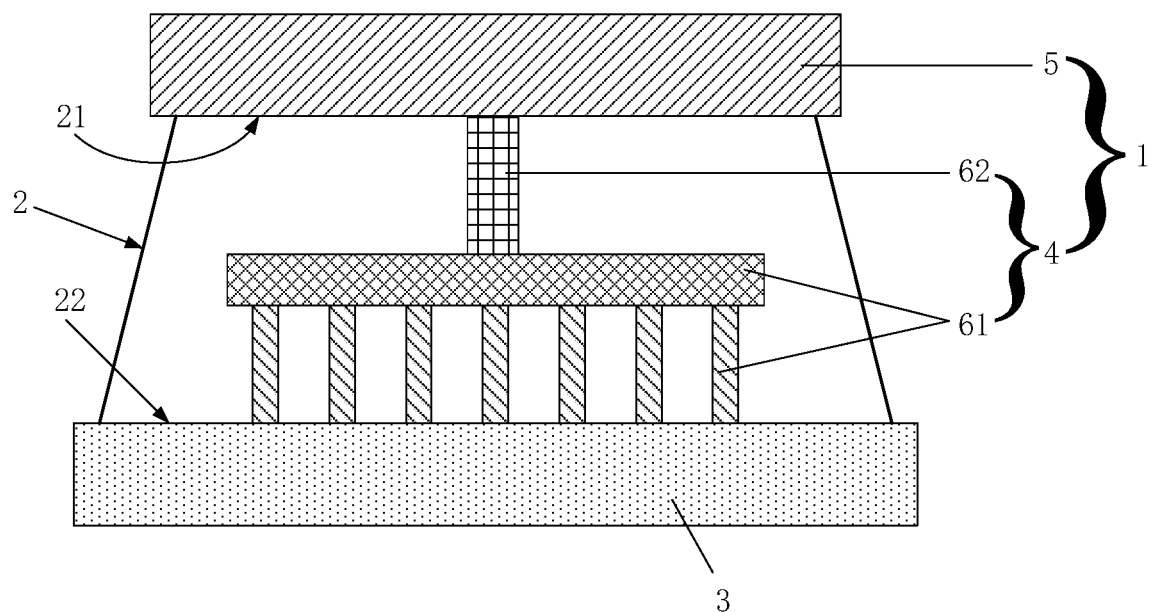
FIG. 1 is a cross-sectional structural schematic view of a brainwave signal collecting device in a use state according to an embodiment of the present disclosure.
Figure 2:
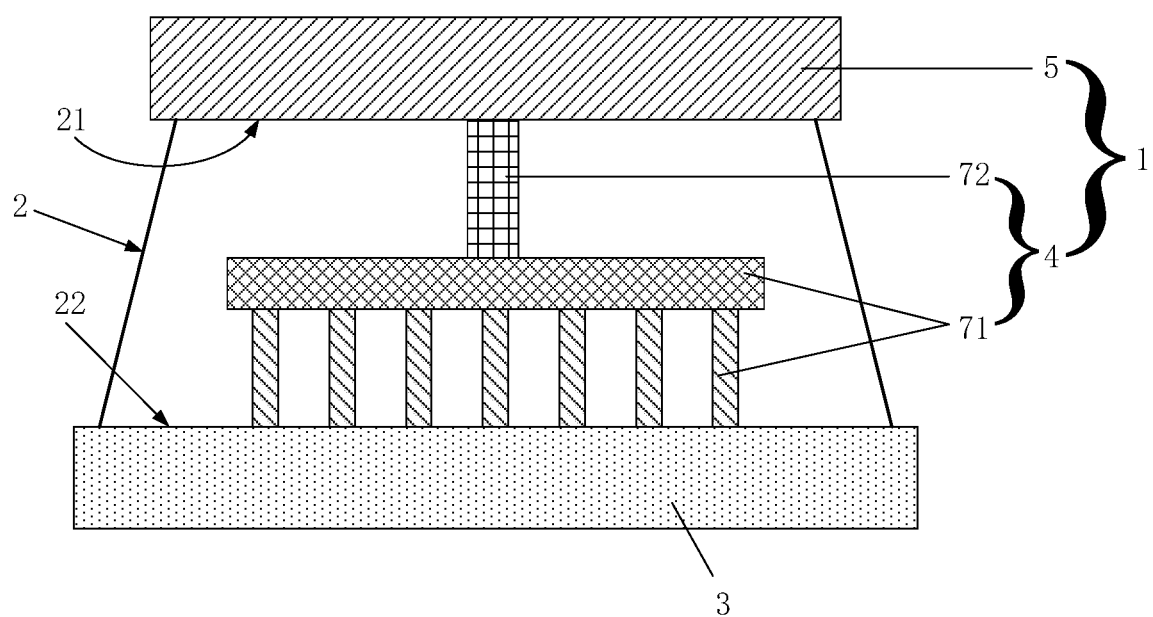
FIG. 2 is a cross-sectional structural schematic view of a brainwave signal collecting device in a use state according to another embodiment of the present disclosure.
Figure 3:
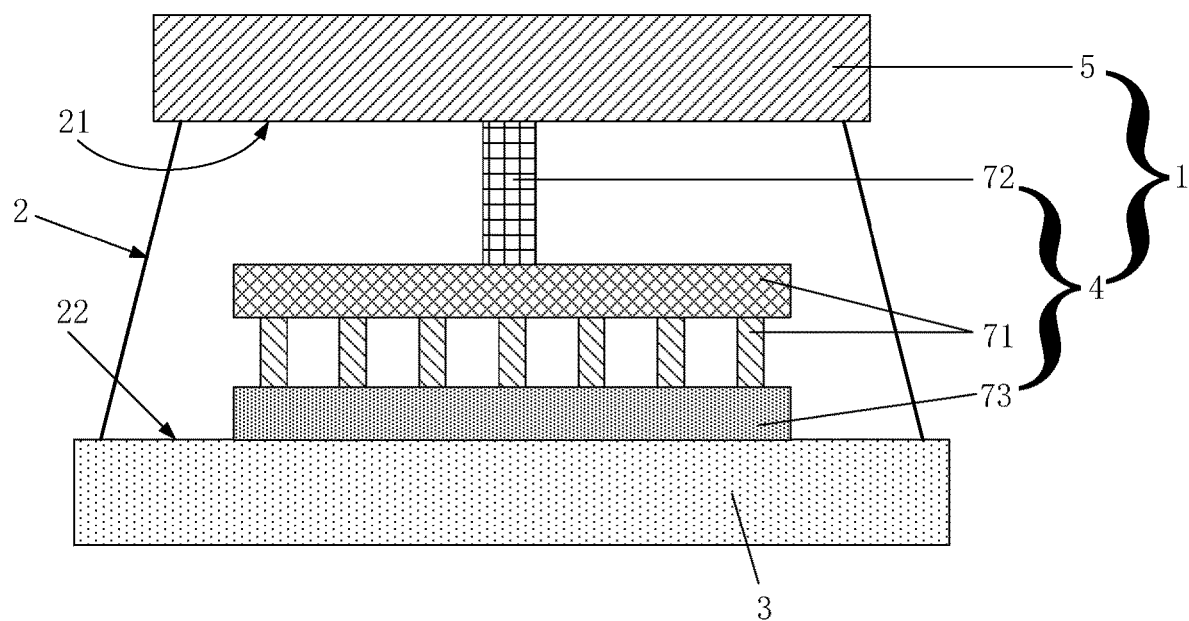
FIG. 3 is a cross-sectional structural schematic view of a brainwave signal collecting device in a use state according to a further embodiment of the present disclosure.

As shown in FIG. 1 to FIG. 3, the brainwave signal collecting device provided by the present disclosure comprises: a main part 1; and an elastic sleeve having a first opening 22, the main part 1 installed on the elastic sleeve, and the elastic sleeve configured to be adsorbed positioned by suction on a head 3 of a user by its first opening 22 after being pressed and make the main part 1 in contact with the head 3 to collect brainwave signals.

In the brainwave signal collecting device provided by the present disclosure, the elastic sleeve is a flexible piece, such as a leather sleeve or a rubber sleeve. Hereinafter, the elastic leather sleeve is used as an example of the elastic sleeve for illustration. When the brainwave signal collecting device is worn, the elastic leather sleeve 2 can be pressed to partly exhaust the air in the elastic leather sleeve 2 so as to be positioned by suction on the head 3 by the first opening 22 of the elastic leather sleeve 2, which can improve the comfort of the head 3 in contact with the elastic leather sleeve 2; and moreover, the position and angle at which the main part 1 contacts the head 3 can be adjusted through the deformation of the elastic leather sleeve 2, which can improve the comfort of the head 3 in contact with the main part 1.

In certain exemplary embodiments, as shown in FIG. 1 to FIG. 3, the main part 1 comprises a brainwave signal collecting unit 4 located in the elastic leather sleeve 2; and a brainwave signal processing unit 5 electrically connected with the brainwave signal collecting unit 4. The brainwave signal collecting unit 4 may be elastically deformable and is in contact with the head 3 to collect the brainwave signals. The angle and position of the brainwave signal collecting unit 4 when contacts the head 3 can be adjusted, so as to reduce the discomfort caused by the contact between the brainwave signal collecting unit 4 and the head 3.

Of course, the specific structure of the main part 1 can also be as follows: the brainwave signal collecting unit 4 is installed in the elastic leather sleeve 2, but the brainwave signal processing unit 5 does not belong to the brainwave signal collecting device and the brainwave signal processing unit 5 is disposed outside the elastic leather sleeve 2, they are electrically connected to each other by, e.g., a wire or a wireless signal. This structure can realize the object of the present application without departing from the design concept of the present disclosure, and also fall within the scope of the present application, which will not be reiterated herein.

In the first specific embodiment of the present disclosure, as shown in FIG. 1, the brainwave signal collecting unit 4 comprises: a carbon nanotube array 61 for collecting the brainwave signals; and a spring 62 having two ends, wherein one end of the spring is electrically connected with the carbon nanotube array 61, and the other end of the spring is electrically connected with the brainwave signal processing unit 5.

A carbon nanotube has a high co-efficient of conductivity, and the array structure formed thereby contacts the head 3 well. The part that connects the carbon nanotube array 61 and the brainwave signal processing unit 5 is a spring 62.

After the brainwave signal collecting device is worn, the carbon nanotube array 61 when abutting against the head 3 can contact the head 3 well, and the elasticity of the spring 62 functions to reduce vibration, so that a user will not feel uncomfortable, and the carbon nanotube array 61 contacts the head 3 well so as to make the brainwave signal collection more accurate and reliable.

In the second embodiment of the present disclosure, as shown in FIG. 2, the brainwave signal collection unit 4 comprises: a spring array 71 for collecting the brainwave signals; and a first electrically conductive piece 72 having two ends, wherein one end of the first electrically conductive piece 72 is electrically connected with the spring array 71, and the other end of the first electrically conductive piece is electrically connected with the brainwave signal processing unit 5. After the brainwave signal collecting device is worn, the spring array 71 when abutting against the head 3 can contact the head 3 well, and the elasticity of the spring array 71 functions to reduce vibration, so that a user will not feel uncomfortable, and the spring array 71 contacts the head 3 well so as to make the brainwave signal collection more accurate and reliable.

Moreover, as shown in FIG. 3, the brainwave signal collecting unit 4 further comprises: a second electrically conductive piece 73 installed on the spring array 71 that collects the brainwave signals through the second electrically conductive piece 73.

Wherein, the first electrically conductive piece 72 and the second electrically conductive piece 73 can be rigid electrically conductive pieces or elastic electrically conductive pieces. They can all realize the object of the present application without departing from the design concept of the present disclosure and fall within the scope of the present application, which will not be reiterated herein.

Figure 4:
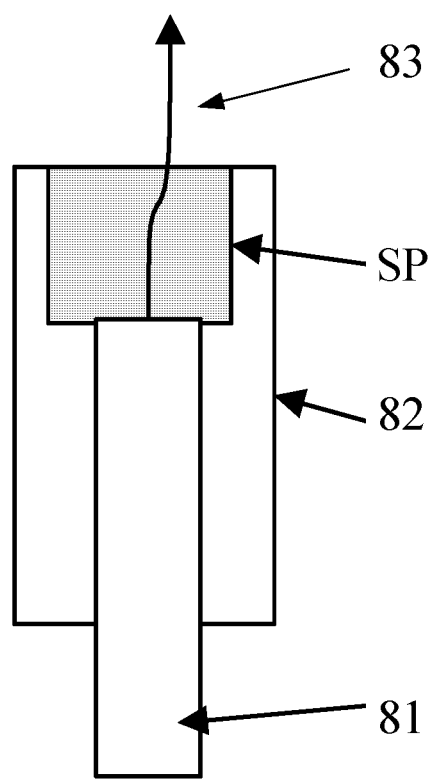
FIG. 4 is a structural schematic view of the first electrically conductive piece of FIG. 2 or FIG. 3 when the first electrically conductive piece is an electrically conductive electrode.

As shown in FIG. 4, the first electrically conductive piece 72 and/or the second electrically conductive piece 73 are electrically conductive electrodes, and the electrically conductive electrode comprises: an electrode body 81; a protective sleeve 82 having a top wall, one end of the electrode body 81 extending into the protective sleeve 82 and the other end thereof being located outside the protective sleeve 82; a spring SP located in the protective sleeve 82 and connected with the top wall of the protective sleeve 82 and the end of the electrode body 81 extending into the protective sleeve 82; and a wire 83 with one end located externally of the protective sleeve 82 so as to be electrically connected to the brainwave signal processing unit 5 and the other end extending through the top wall of the protective sleeve 82 so as to be electrically connected with the end of the electrode body 81 extending into the protective sleeve 82, wherein the protective sleeve 82 is, on the one hand, used for protecting the electrode body 81, and, on the other hand, used for adjusting the spring SP so as to adjust the fitting degree of the electrode body 81 and the head 3.

Of course, the first electrically conductive piece 72 and/or the second electrically conductive piece 73 can also be resilient conductive piece. The resilient conductive piece per se works as a conductor, or can be additionally provided with a wire serving as a conductor. Both can realize the object of the present application without departing from the design concept of the present disclosure and fall within the scope of the present application, which will not be reiterated herein.

In certain exemplary embodiments, the brainwave signal processing unit 5 is a brainwave signal processing circuit (having such functions as noise reduction and signal amplification). The material of the elastic sleeve 2 is rubber or leather, which is light-weighted and can reduce the burden on a head.

Wherein, the brainwave signal processing unit is located inside or outside the rubber sleeve (not shown). It is also possible that, as shown in FIG. 2, the rubber sleeve has a second opening 21 encapsulated by the brainwave signal processing circuit, so as to prevent the rubber sleeve from falling off the head due to gas leakage.

All the three manners can realize the object of the present application without departing from the design concept of the present disclosure and fall within the scope of the present application, which will not be reiterated herein.

In the brainwave signal collecting device provided by the present disclosure, the elastic leather sleeve is directly sleeved onto the head so that the main part contacts the head to collect the brainwave signals. There is no need for a patient to have his head shaved.

To sum up, the brainwave signal collecting device provided by the present disclosure has an elastic leather sleeve serving as a flexible piece. When the brainwave signal collecting device is worn, the elastic leather sleeve can be pressed to partly exhaust the air therein so as to be positioned by suction on the head through the first opening 22 of the elastic leather sleeve, which can improve the comfort of the head in contact with the elastic leather sleeve; and moreover, the position and angle at which the main part contacts the head can be adjusted through the deformation of the elastic leather sleeve, which can improve the comfort of the head in contacts with the main part.

In the depiction herein, the terms such as "installed", "connected", "coupled" and "secured" shall be understood in a broad sense. For example, "connected" can be fixedly connected, removably connected or integrally connected; or can be directly connected or indirectly connected by an intermediate medium. As far as those ordinarily skilled in the art are concerned, the specific meanings of those terms shall be understood under particular circumstances.

In the depiction herein, the terms such as "an embodiment", "some embodiments" and "specific embodiments" indicate that specific features, structures, materials or characteristics described in combination with the embodiment or example shall be contained in at least one embodiment or example of the present disclosure. In the description, exemplary depiction of those terms does not necessarily refer to the same embodiments or examples. The described specific features, structures, materials or characteristics can be combined in a suitable manner in any one or more embodiments or examples.

Although the description discloses the embodiments as stated above, those contents are only embodiments adopted for easy understanding of the present disclosure, and not intended to impose any limitation to the present disclosure. Any person skilled in the art can make any modification and change to the implemented form and details without departing from the spirit and scope of the present disclosure. However, the scope of the present disclosure shall depend on the scope defined by the appended claims.

The invention claimed is:

1. A brainwave signal collecting device, comprising:
   a main part; and
   an elastic sleeve having a first opening and a second opening, wherein the main part is installed to the elastic sleeve, and the elastic sleeve is configured to be positioned by suction on a head of a user through the first opening,
   wherein the main part is configured to contact the head to collect brainwave signals,
   wherein the main part comprises:
   a brainwave signal collecting unit located in the elastic sleeve; and
   a brainwave signal processing unit electrically connected with the brainwave signal collecting unit,
   wherein the second opening is covered by the brainwave signal processing unit,
   wherein the brainwave signal collecting unit comprises:
   a spring array for collecting the brainwave signals;
   a first electrically conductive piece having two ends, wherein one end of the first electrically conductive piece is electrically connected with the spring array, and the other end of the first electrically conductive piece is electrically connected with the brainwave signal processing unit; and
   a second electrically conductive piece which is an electrically conductive spring and is installed on the spring array, wherein the spring array is configured to collect the brainwave signals through the second electrically conductive piece, and
   wherein the first electrically conductive piece is an electrically conductive electrode comprising:
   an electrode body;
   a protective sleeve having a top wall, one end of the electrode body extending into the protective sleeve and another end of the electrode body being located outside the protective sleeve;
   a spring located in the protective sleeve and connected with the top wall of the protective sleeve and the end of the electrode body extending into the protective sleeve; and
   a wire with one end thereof located externally of the protective sleeve and the other end thereof extended through the top wall of the protective sleeve so as to be electrically connected with the end of the electrode body extending into the protective sleeve.

2. The brainwave signal collecting device according to claim 1, wherein the brainwave signal processing unit is a brainwave signal processing circuit, and a material of the elastic sleeve is rubber or leather.

3. The brainwave signal collecting device according to claim 2, wherein the brainwave signal processing circuit is located inside or outside the sleeve.

* * * * *